United States Patent [19]

Taban

[11] Patent Number: 4,516,570

[45] Date of Patent: May 14, 1985

[54] PESSARY

[76] Inventor: Charles H. Taban, 50bis Ch des Falquet, 1223 Cologny, Switzerland

[21] Appl. No.: 412,162

[22] Filed: Aug. 27, 1982

[51] Int. Cl.³ .............................................. A61F 5/46
[52] U.S. Cl. .................................................... 128/130
[58] Field of Search ....................... 128/127, 130, 131

[56] References Cited

U.S. PATENT DOCUMENTS

| | | | |
|---|---|---|---|
| 2,574,767 | 11/1957 | Stubbs | 128/127 |
| 4,066,075 | 1/1978 | Hughes | 128/127 |
| 4,182,321 | 1/1980 | Csatary | 128/130 |

Primary Examiner—Stephen C. Pellegrino
Attorney, Agent, or Firm—Vorys, Sater, Seymour and Pease

[57] ABSTRACT

A foldable prolapse pessary having a maleable metal core hermetically covered by a flexible, bio-compatible polymeric material.

1 Claim, 3 Drawing Figures

U.S. Patent  May 14, 1985  4,516,570
FIG. I.
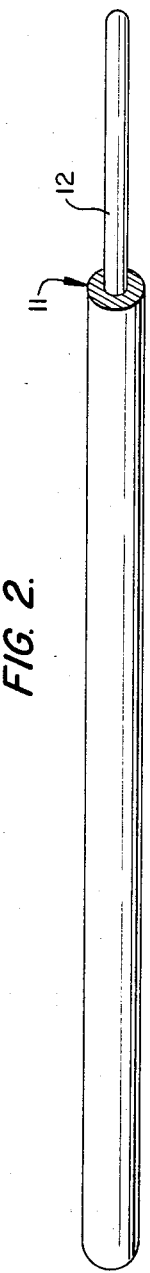
FIG. 2.
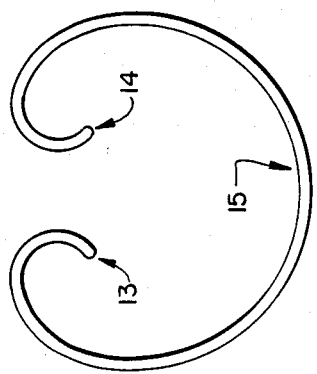
FIG. 3.

PESSARY

BACKGROUND OF THE INVENTION

This invention relates to pessaries and more particularly to pessaries of specialized shape for use by gynecologists in treating uterine and/or vaginal prolapse.

In recent years there has been a marked increase in the number of women afflicted with uterine and/or vaginal prolapse due in part to the increase in the population of middle aged and older women. In many cases it is inadvisable to correct such conditions in women by surgery because of a variety of reasons including the age of the patient, her generally poor physical condition, or for psychological reasons. In such cases the treatment requires the use of a mechanical support in the form of a pessary which provides an artificial perineal support. There are a number of prolapsus pessaries known and used in the art, and they are available in a variety of shapes, caliber, and materials. But for the most part they are characterized by a free-form, generally rigid configuration. Because the physical structure and type, as well as the degree of prolapse, varies from one individual to another, the insertion of a prior art pessary usually necessitates tests using a number of devices of varying shapes and caliber. For the gynecologist often overloaded with work, such a trial and error method presents disadvantages and for the patient the required procedure tends to be uncomfortable and at least inconvenient.

SUMMARY OF THE INVENTION

Therefore, it is the object of the invention to provide a pessary which can be rapidly inserted without inconvenience or adverse effects to the patient.

According to this invention, a pessary is provided comprising a central unitary core of solid malleable wire of sufficient size and strength to effectively provide perineal support in a patient and a coating of synthetic, pliable, biocompatible polymeric material hermetically sealing the core material. The pessary of this invention may be produced in a closed ring form or in an open arrangement.

BRIEF DESCRIPTION OF THE DRAWINGS

The invention will be better understood upon reference to the following description and the accompanying drawings in which:

FIG. 1 is a perspective view illustrating an embodiment of this invention in its folded or collapsed arrangement to facilitate insertion.

FIG. 2 is a sectional view of the pessary illustrated in FIG. 1 with a portion broken away to show the underlining maleable core.

FIG. 3 is a perspective view of an open embodiment of the invention in the form in which it would exist when inserted into the vaginal anatomy.

DESCRIPTION OF THE INVENTION

Referring to the accompanying drawings, the pessary shown in FIGS. 1 and 2 is folded into a narrow configuration so that it may be introduced into the vagina without discomfort to the patient. Upon insertion it may be shaped to an appropriate fit by the attending physician. This initial insertion of the pessary will normally be followed by one or two checkups by the physician which can be spaced out over gradually lengthening intervals. Removal of the pessary for cleaning is accomplished in a manner which is the reverse of insertion, that is to say the pessary is folded inside the vagina and then extracted without pain or damage because of the reduced diameter of the device.

In a preferred embodiment, the outside circumference of the pessary will be about 285 mm and its overall diameter will be preferably about 10 mm. In FIG. 2, the enveloping bio-compatible polymeric sheath 11, which may be formed from any suitable, pliable polymer material, such as polypropylene-polyethylene is cut away to reveal the central malleable metal core 12. In the preferred embodiment, the sheath will be about 2 mm thick and the diameter of the metal core is about 3 mm. The metal core may be formed from any malleable metal, although copper is the preferred element.

It is important to know that the core is totally enveloped and hermetically sealed in the flexible sheath. Such sealing may be accomplished by any known means such as by heating, by ultrasonic means, or by molding.

The embodiment of the pessary of this invention illustrated in the drawings has a first free end 13, a second free end 14, and an intermediate portion 15, located between the two free ends. In the embodiment illustrated in FIG. 3, the intermediate portion 15 of the pessary is formed into a semicircular shape, the semicircle having a center and a radius. Each free end, 13 and 14 is curved or looped inward toward the center of the semicircle, each free end having a radius of curvature smaller than the radius of the semicircle represented by the intermediate portion of the pessary.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

One of the most important features of this invention is its adjustability in all directions, due in large part to the nature of the pliable, i.e. semi-rigid, sheath referred to above. This allows the physician to be unimpeded in adjusting the pessary to the patient's individual needs.

I claim:

1. A pessary comprising a unitary malleable metal core member, and a flexible sheath hermetically covering said core member, said sheath being formed from a bio-compatible polymeric material, said pessary having a first free end, a second free end and an intermediate portion between said free ends, and said pessary being formed into a non-closed curve wherein said intermediate portion has a generally semicircular shape, said semicircle having a center and a radius, and said free ends being curved inward generally toward said center, said free ends having radii of curvature smaller than the radius of said semicircle.

* * * * *